US006316424B1

(12) United States Patent
Dadey et al.

(10) Patent No.: US 6,316,424 B1
(45) Date of Patent: Nov. 13, 2001

(54) SULFATED PHOSPHATIDYLINOSITOLS, THEIR PREPARATION AND USE OF THE SAME

(75) Inventors: Eric J. Dadey, Aurora; Xiao-Hui Mei, Chicago, both of IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/483,150

(22) Filed: Jan. 14, 2000

Related U.S. Application Data

(60) Provisional application No. 60/116,166, filed on Jan. 15, 1999.

(51) Int. Cl.$^7$ .................................................. A61K 31/70
(52) U.S. Cl. .................................................... 514/48
(58) Field of Search ................................................ 514/48

(56) References Cited

U.S. PATENT DOCUMENTS 5,194,654 * 3/1993 Hostetter et al. ..................... 558/152

FOREIGN PATENT DOCUMENTS

| 2255070 | 11/1997 | (CA) . | |
|---|---|---|---|
| 0 293 826 | 12/1988 | (EP) | A61K/31/725 |
| WO 93/21191 | 10/1993 | (WO) | C07F/9/10 |

OTHER PUBLICATIONS

Yoshida et al., "Sulfation of the immunomodulating polysaccharide lentinan: A novel strategy for antivirals to human immunodeficiency virus (HIV)," *Biochemical Pharmacology*, vol. 37, No. 15, pp. 2887–2981 (1988).

Weislow et al., "New soluble–formazan assay for HIV–1 cytopathic effects: Application to high–flux screening of synthetic and natural products for ADIS–antiviral activity, " *Journal of the National Cancer Institute*, vol. 81, No. 8, pp. 577–586 (1989).

Gustafson et al., "AIDS–antiviral sulfolipids from cyanobateria (blue–green algae)," *Journal of the National Cancer Institute*, vol. 81, No. 16, pp. 1254–1258 (1989).

Baba et al., "Novel sulfated polymers as highly potent and selective inhibitors of human immunodeficiency virus replication and giant cell formation," *Antimicrobial Agents and Chemotherapy*, vol. 34, No. 1, pp. 134–138 (1990).

Mohan, et al., "Sulfonic acid polymers as a new class of human immunodeficiency virus inhibitors," *Antiviral Research*, pp. 139–150 (1992).

Bàrzu et al., "Preparation and anti–HIV activity of O–acylated heparin and dermatan sulfate derivatives with low anticoagulant effect," *J. Med. Chem.*, 36, pp. 3546–3555 (1993).

Harrop et al., "Heparin and its derivaties bind to HIV–1 recombinant envelope glycoproteins, rather than to recombinant HIV–1 receptor, CD4," *Glycobiology*, vol. 8, No. 2, pp. 131–137 (1998).

Ohta et al.,Sulfoquinovosyldiacylglycerol, KM043, a new potent inhibitor of eukaryotic DNA polymerases and HIV–reverse transcriptase type 1 from a marine red alga, *Gigartina tenella, Chem. Pharm. Bull.*, pp. 684–686 (1998).

\* cited by examiner

*Primary Examiner*—Zohreh Fay
(74) *Attorney, Agent, or Firm*—Marshall, Gerstein & Borun

(57) ABSTRACT

A sulfated phosphatidylinositol, pharmaceutical compositions containing a sulfated phosphatidylinositol, and the administration of a sulfated phosphatidylinositol or the pharmaceutical compositions to individuals are disclosed. A sulfated phosphatidylinositol can be used alone to elicit a pharmacologic response, or can be incorporated into a variety of pharmaceutical compositions, both liquid and solid, as a component of a drug delivery system for the administration of a therapeutic agent to an individual.

34 Claims, 8 Drawing Sheets

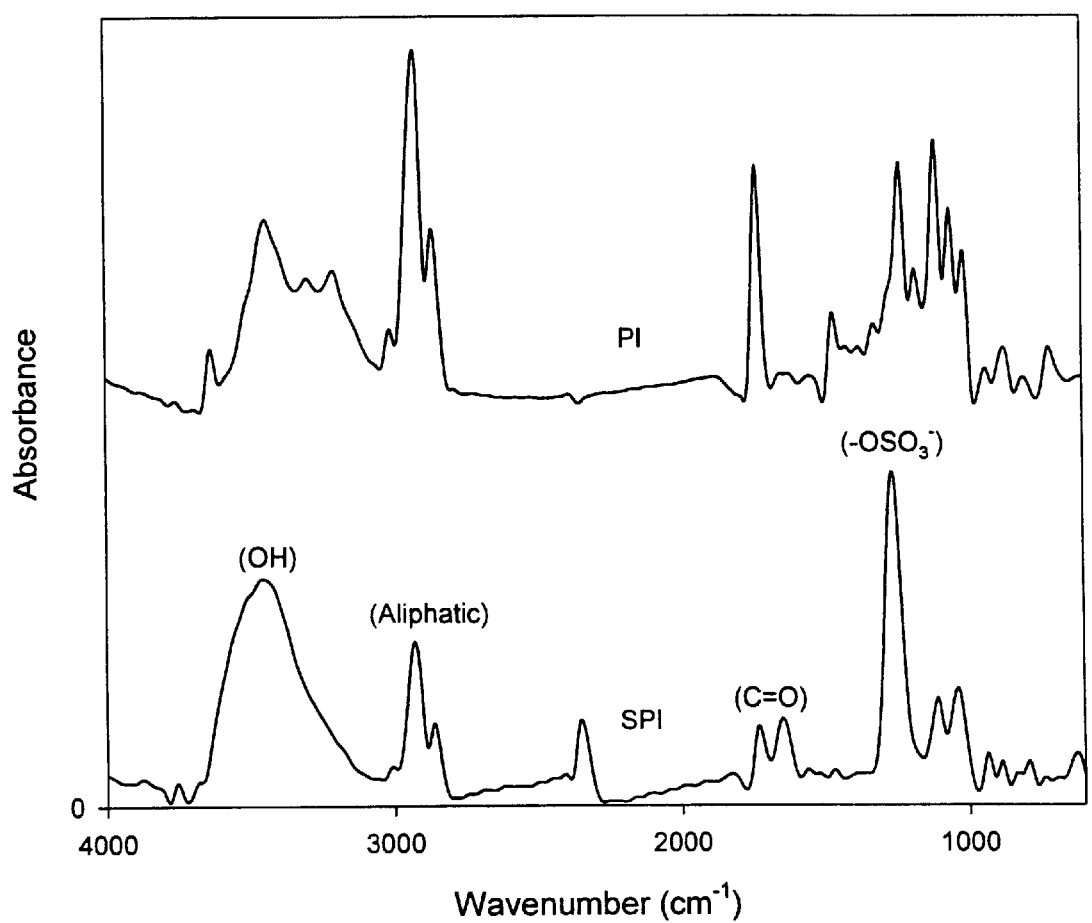
Figure 1. FT-IR Spectra of SPI and PI.

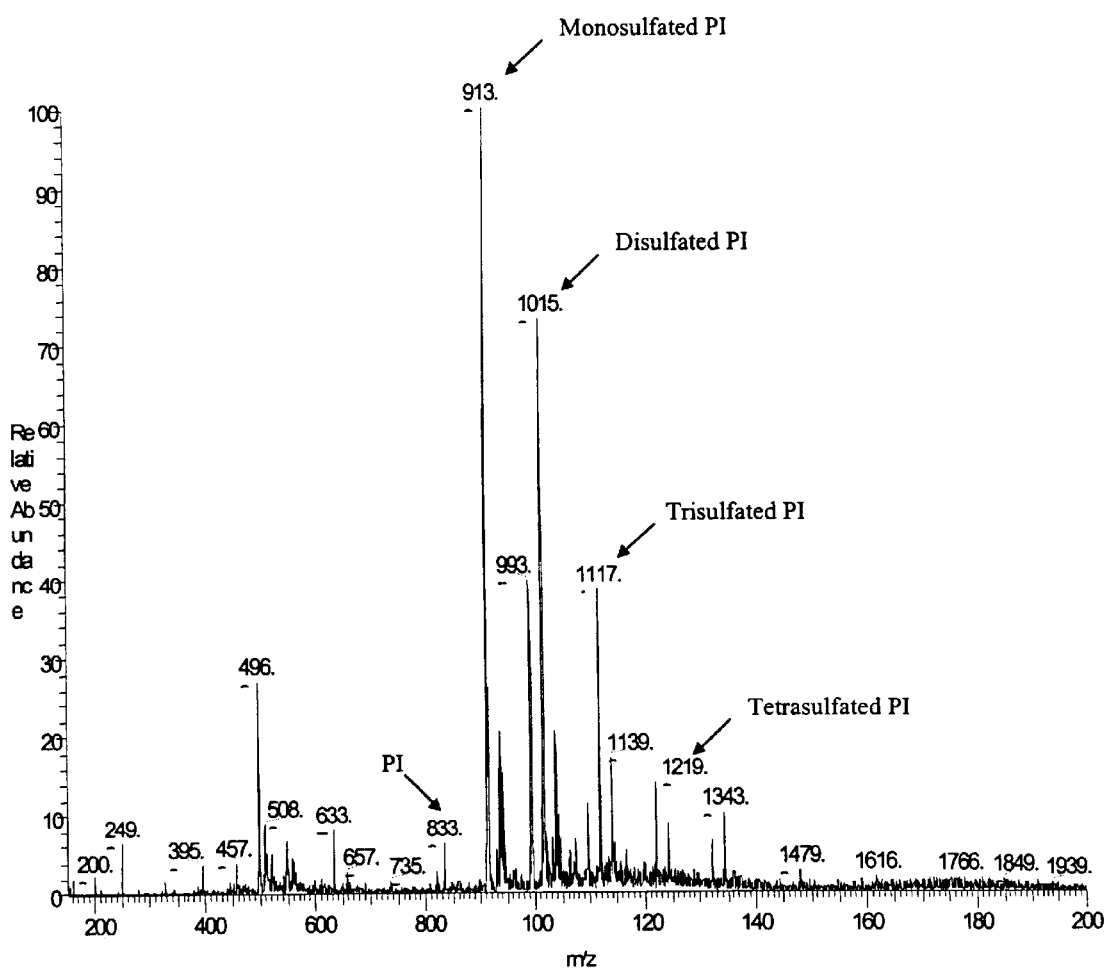
Figure 2. Mass Spectrum of SPI.

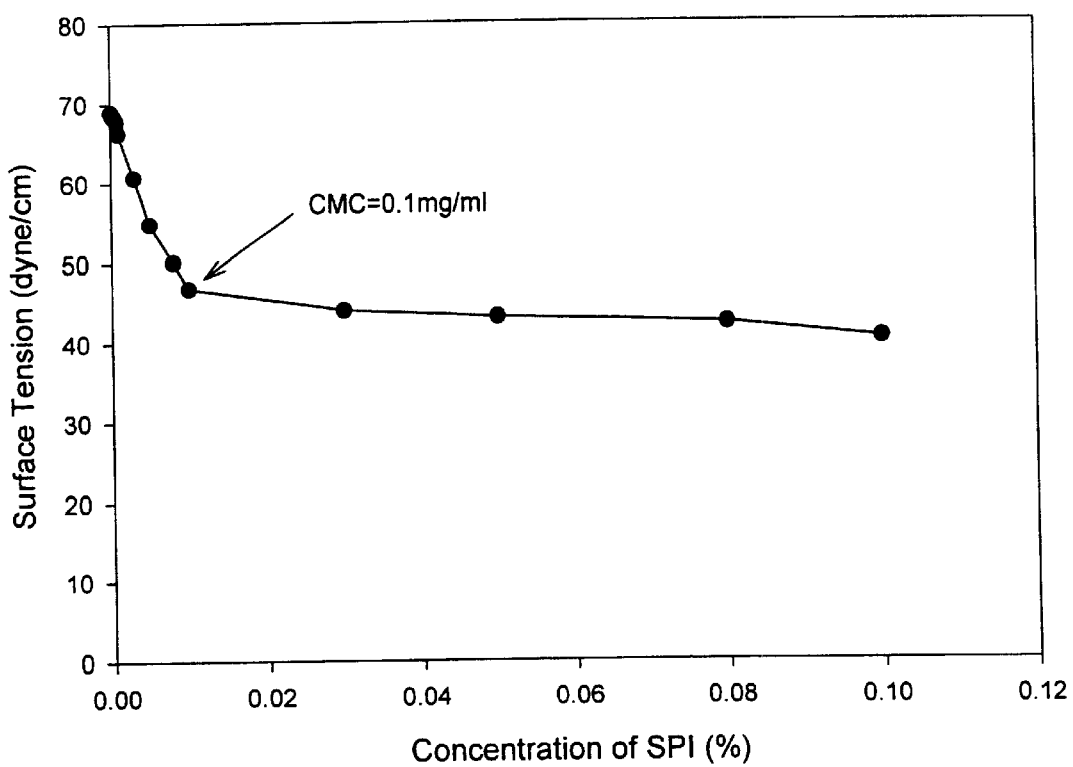
Figure 3. Surface Activity of SPI.

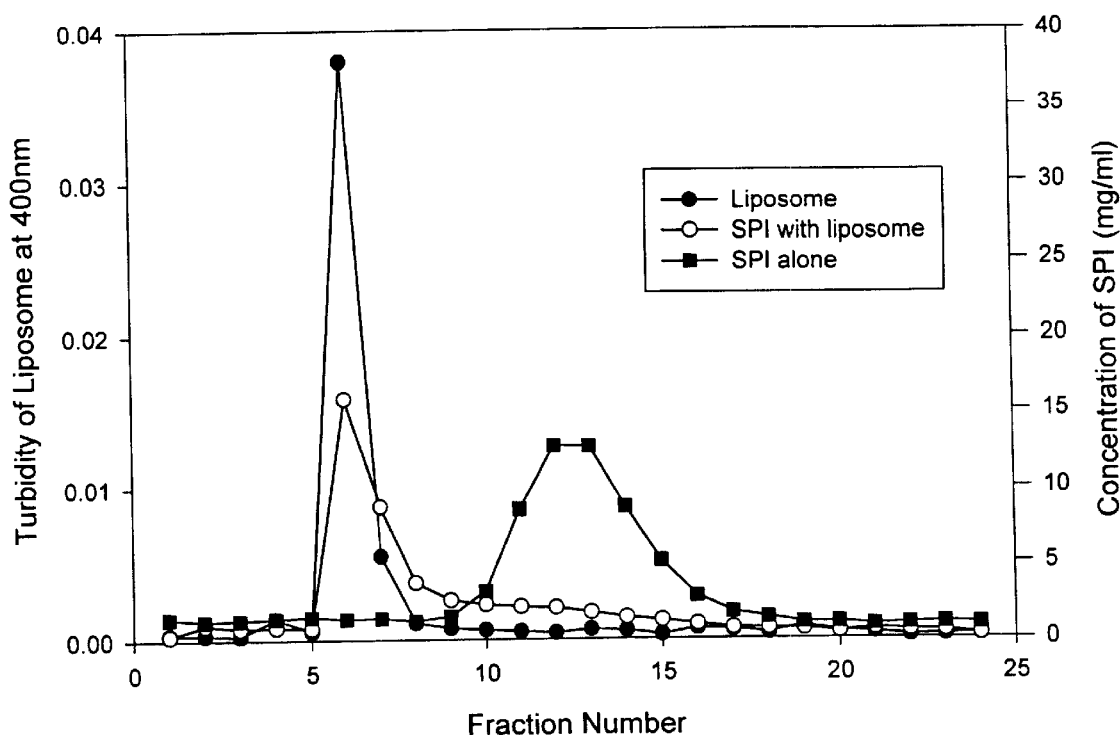
Figure 4. Gel Permeation Chromatography of PSL.

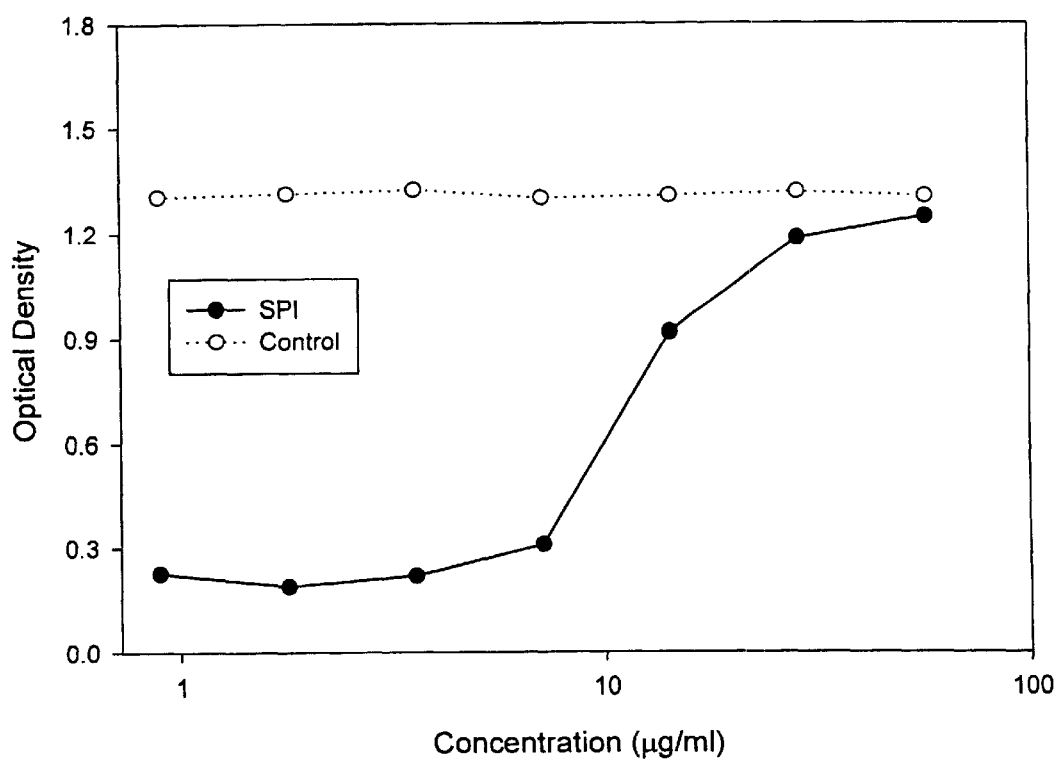
Figure 5. Inhibition of HIV Cytopathicity by SPI.

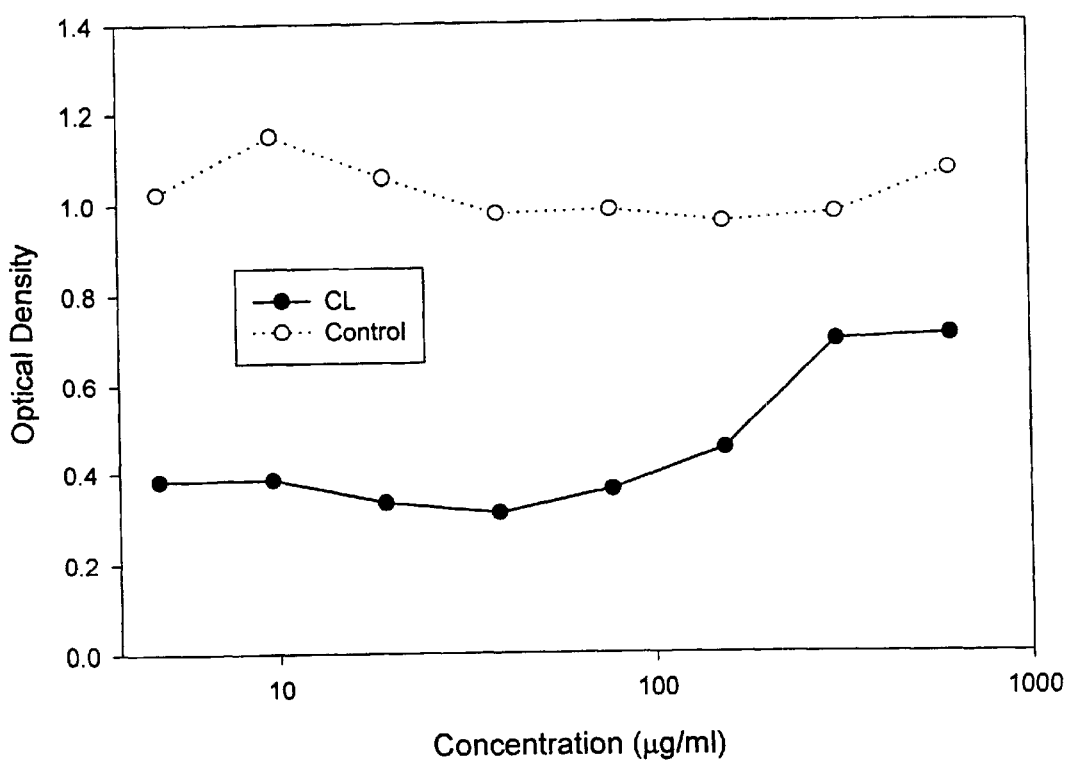
Figure 6. Inhibition of HIV Cytopathicity by Conventional Liposome.

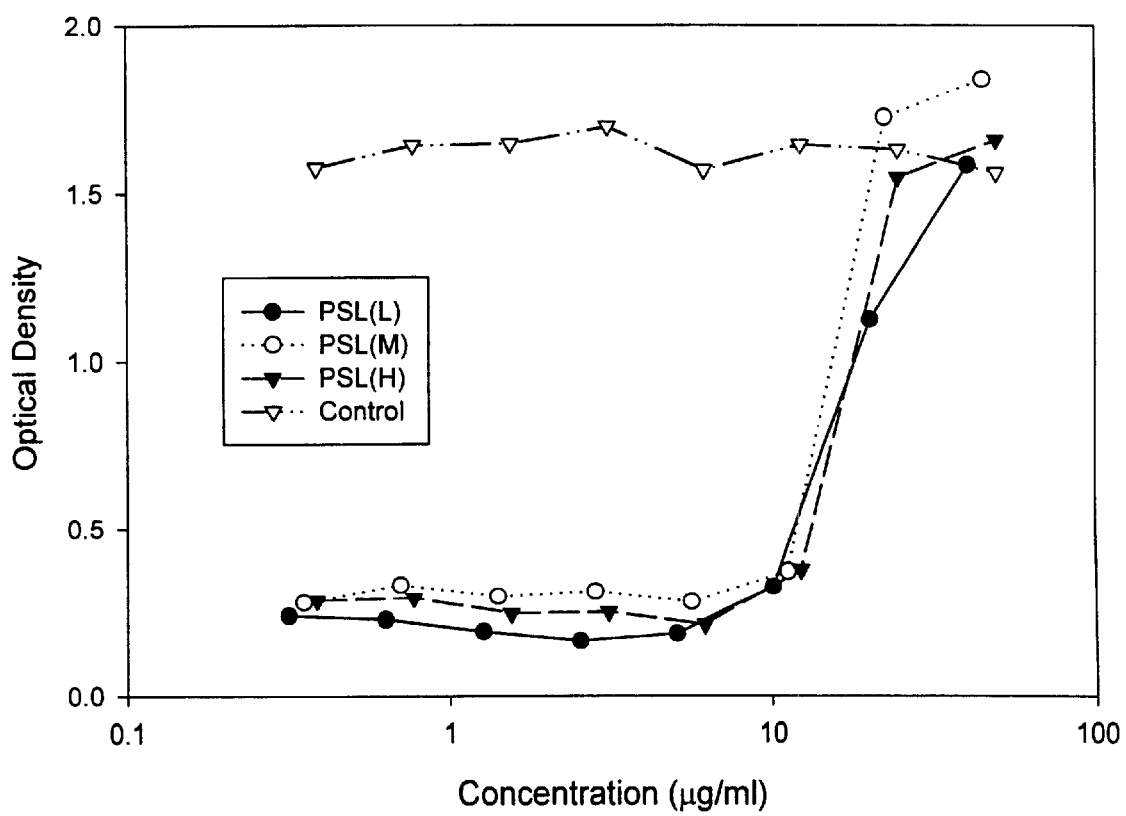
Figure 7. Inhibition of HIV Cytopathicity by PSLs.

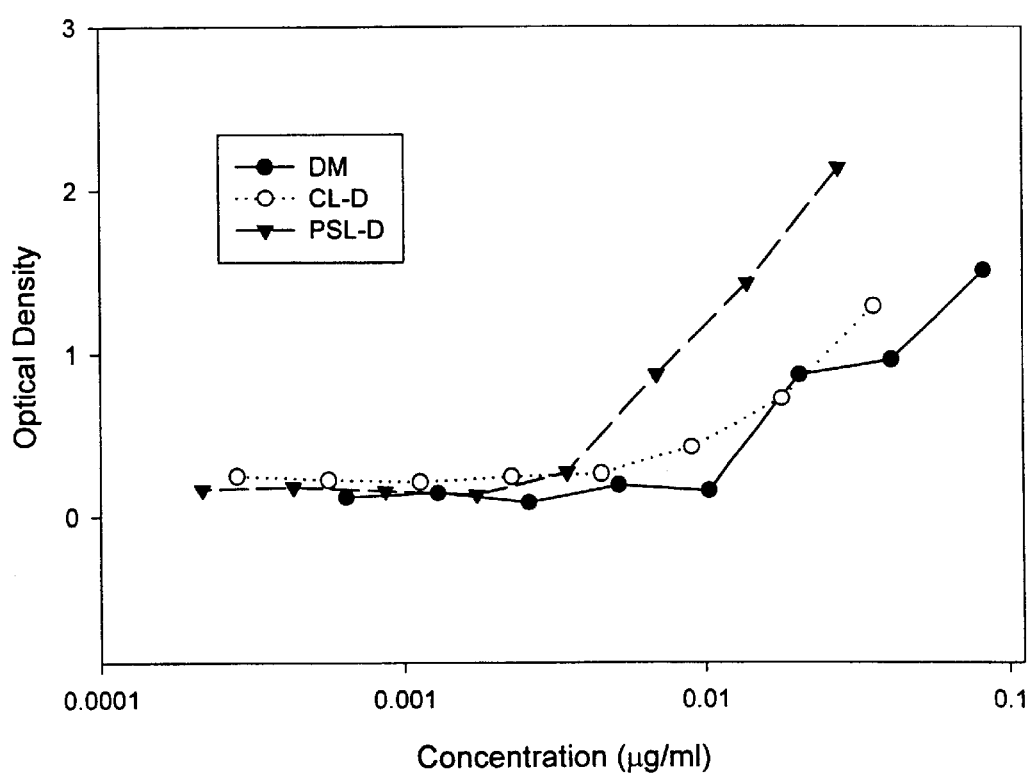
Figure 8. Inhibition of HIV Cytopathicity by Delavirdine, Conventional Liposome and Polysulfated Liposome Containing Delavirdine.

SULFATED PHOSPHATIDYLINOSITOLS, THEIR PREPARATION AND USE OF THE SAME

CROSS-REFERENCE TO RELATED APPLICATIONS

This application claims the benefit of provisional application Ser. No. 60/116,166, filed Jan. 15, 1999.

FIELD OF THE INVENTION

The present invention relates to sulfated phosphatidylinositols, and their use in therapy or as a component of a drug delivery system for a therapeutic agent. More particularly, the present invention relates to the preparation and characterization of sulfated phosphatidylinositols, and their use in pharmaceutical compositions and in methods of treating a disease.

BACKGROUND OF THE INVENTION

A variety of sulfated polymers exhibit antiviral activity against human immunodeficiency virus (HIV). Baba et al., *Antimicrobial Agents and Chemotherapy*, 34(1), 134–138 (1990), discloses using sulfated polyvinyl alcohol, dextran sulfate, or a sulfated copolymer of acrylic acid and vinyl alcohol to inhibit HIV replication and giant cell formation. In similar studies, Mohan et al., *Antiviral Research*, 18, 139–150 (1992), discloses sulfonic acid polymers, such as poly(4-styrenesulfonic acid), poly(anetholesulfonic acid), poly(vinylsulfonic acid), poly(2-acrylamido-2-methyl-l-propanesulfonic acid), and dextran sulfate, to inhibit HIV and syncytium formation. Other investigators prepared curdlan galactose sulfate, curdlan arabinose sulfate, and lentinan sulfate from respective, nonsulfated polysaccharides. In vitro studies revealed that these sulfated polysaccharides inhibit HIV infection, block cell-fusion events, and inhibit reverse transcriptase (RT) activity (see Yoshida et al., *Biochemical Pharmacology*, 37(15), 2887–2891 (1988)).

Other investigators (see, for example, Gustafson et al., *J. Nat. Can. Inst.*, 81(16), 1254–1258 (1989), and Ohta et al., *Chem. Pharm. Bull.*, 46(4), 684–686 (1998)) found that certain sulfolipids inhibited the cytopathic effects of the HIV virus and inhibited syncytium formation. However, these sulfolipids are natural products, which are isolated from marine algae using a cumbersome process to yield small amounts of sulfolipid. For example, a relatively large amount of algae (e.g., 300 grams (g) dry weight) is collected, and the sulfolipid is extracted from the algae using organic solvents, then purified. This process provides about 3.1 milligrams (mg) of the purified sulfolipid for an overall yield of 0.0010%. In yet another study, Barzu et al., *J. Med. Chem.*, 36, 3546–3555 (1993), discloses that naturally occurring sulfated polysaccharides, such as heparin, dermatan sulfate, and several chemically modified heparins, inhibited giant-cell formation normally associated with HIV infection.

Accordingly, polymers and polysaccharides having a plurality of sulfur-containing acid groups have demonstrated a positive antiviral effect on HIV in vitro. Harrop et al., *Glycobiology*, 8(2), 131–137 (1998), explains this behavior by showing that radiolabelled heparin, which is a naturally occurring sulfated polysaccharide, binds to specific glycoproteins on the viral envelope, thereby inhibiting the human immunodeficiency virus from binding to its natural host cell receptor, CD4.

Although the above-discussed sulfated polymers and polysaccharides showed promise in vitro, therapeutic responses in vivo were disappointing. A significant number of the sulfated polymeric materials are not only cost prohibitive, but also exhibit a low efficacy and a low bioavailability in vivo when administered intravenously. The sulfated polymeric materials also demonstrate a strong, undesirable anticoagulant effect. Accordingly, it would be an advance in the art to provide a compound that demonstrates the therapeutic, e.g., antiviral, advantages of sulfated polymeric materials, while overcoming their disadvantages, in the management of AIDS, for example. The present invention is directed to such compounds.

SUMMARY OF THE INVENTION

The present invention is directed to sulfated phosphatidylinositols and their use in therapy. More particularly, the present invention is directed to the preparation and characterization of sulfated phosphatidylinositols having the idealized structure (I), wherein each R, independently, is H, $SO_3H$, or $SO^-_3$,

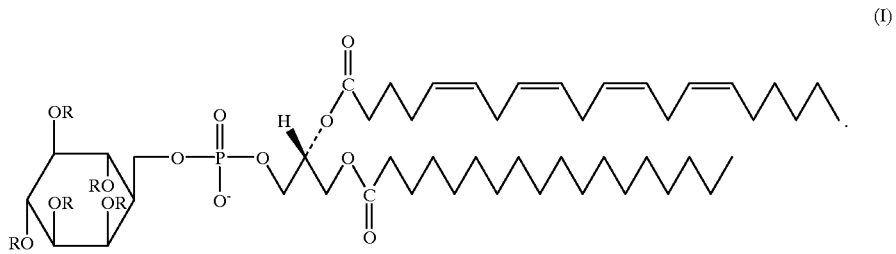

(I)

Therefore, one aspect of the present invention is the preparation and characterization of sulfated phosphatidylinositols.

Another aspect of the present invention is the use of a sulfated phosphatidylinositol in therapy to treat a disease. The sulfated phosphatidylinositols can be used as the active agent to treat the disease, or as a component of a drug delivery system of a pharmaceutical composition which contains an additional therapeutic agent.

Another aspect of the present invention is to provide a pharmaceutical composition that can be administered to an individual to treat an acute or chronic disease.

Another aspect of the present invention is the use of a sulfated phosphatidylinositol as a component of a drug delivery system for a more efficacious delivery of a therapeutic agent to a target site within an individual.

Yet another aspect of the present invention is a method of treating a disease or condition comprising administering to an individual a therapeutically effective amount of a sulfated phosphatidylinositol. The disease or condition, for example, can be the treatment, suppression, or prevention of AIDS.

Yet another aspect of the present invention is to provide a pharmaceutical composition containing a therapeutic agent and a drug delivery system, wherein the drug delivery system comprises a sulfated phosphatidylinositol and an amphiphilic compound, wherein the composition can be administered to an individual in a liquid form, either orally or by injection.

Still another aspect of the present invention is to provide a pharmaceutical composition containing a therapeutic agent and a sulfated phosphatidylinositol in a lyophilized form, such that the therapeutic agent can be administered to an individual in a solid form. Such a solid composition is especially useful for the oral administration of a therapeutic agent to an individual.

Another aspect of the present invention is to provide a pharmaceutical composition containing a therapeutic agent and a sulfated phosphatidylinositol that is site specific for improved delivery of the therapeutic agent and improved treatment of the disease of concern.

Still another aspect of the present invention is to provide a method of treating a disease comprising administering to an individual a therapeutically effective amount of a pharmaceutical composition comprising a drug delivery system and a therapeutic agent. The drug delivery system comprises a sulfated phosphatidylinositol and an amphiphilic compound. The drug delivery system more effectively delivers the therapeutic agent to the target site of interest within the individual.

These and other novel aspects and advantages of the present invention will become apparent from the following detailed description of the preferred embodiments taken in conjunction with the figures.

BRIEF DESCRIPTION OF THE FIGURES

FIG. 1 contains FT-IR spectra of phosphatidylinositol (PI) and sulfated phosphatidylinositol (SPI);

FIG. 2 is a mass spectrum of SPI showing the relative abundance of SPI species;

FIG. 3 is a plot of surface tension (dyne/cm) vs. concentration of SPI (wt. %);

FIG. 4 contains plots of turbidity (400 nm) vs. fraction number for gel permeation chromatograms of a liposome, SPI, and an SPI/liposome; and FIGS. 5–8 are plots of optical density vs. concentration ($\mu$/ml) showing the inhibition of HIV cytopathicity of SPI, a liposome, PSLs, delaviridine, and PSL liposomes containing delaviridine.

DETAILED DESCRIPTION OF THE PREFERRED EMBODIMENTS

The ability of various sulfated polymers to exhibit antiviral activity against HIV is discussed above. The disadvantages associated with such sulfated polymers also has been discussed.

In addition, currently available treatment regimens may utilize a long-term, daily administration of multiple therapeutic agents to treat a variety of diseases, like AIDS, for example. These regimens for treating AIDS, and other diseases, rely on the passive ability of the body to distribute therapeutic agents to target sites. However, by doing so, the entire body, including nonaffected areas, is exposed to the unwanted and potential toxic effects of the therapeutic agents. It would be beneficial, therefore, to provide an efficacious treatment regimen that directs the therapeutic agent to the infected target site, while limiting total body exposure. It should be understood that treatment extends to prophylaxis as well as treatment of established conditions.

As demonstrated herein, the present invention overcomes the disadvantages demonstrated by sulfated polymers in the treatment of HIV and other diseases. In addition, the present invention provides a drug delivery system that more effectively delivers a therapeutic agent to a target site in an individual in the treatment of a disease. Accordingly, the present invention has the benefit of providing a pharmaceutical composition comprising a therapeutic agent and a drug delivery system, wherein the drug delivery system more effectively directs the therapeutic agent to a target site within the individual, and wherein a component of the drug delivery system, i.e., a sulfated phosphatidylinositol, also exhibits therapeutic activity. Accordingly, the drug delivery system and a therapeutic agent behave in a synergistic fashion, thereby lowering the overall dose of the therapeutic agent required to treat the disease, increasing efficacy of the therapeutic agent, and shortening the duration of therapy.

In particular, the present invention discloses the synthesis and characterization of a novel, chemically modified phospholipid termed a sulfated phosphatidylinositol. A sulfated phosphatidylinositol of the present invention is a novel compound that can be used alone to elicit a pharmacologic response, or can be used in a pharmaceutical composition as a component of a drug delivery system for a therapeutic agent. The sulfated phosphatidylinositol-containing composition can be used for administration of therapeutic agents, including, but not limited to, peptides, proteins, antivirals, antibacterials, antifungals, antineoplastics, antiprotozoals, antiarthritics, and antiinflammatory agents to an individual. The drug delivery system can be in the form of a liposome, emulsion, micelle, microemulsion, or mixed micelle, for example.

The sulfated phosphatidylinositols have an idealized structure depicted as structural formula (I), wherein each R, independently, is H, $SO_3H$, or $SO^-_3$. In general, the sulfated phosphatidylinositols

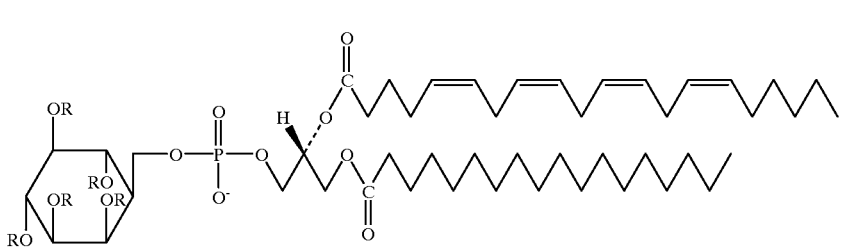

(I)

of structural formula (I) are prepared by reacting the free hydroxyl groups on the sugar moiety (i.e., the inositol moiety) of phosphatidylinositol with a sulfur trioxide/dimethylformamide ($SO_3$/DMF) complex. The sulfated phosphatidylinositol then is isolated, purified, and lyophilized to provide a white amorphous powder.

One or more of the hydroxy groups, therefore, are converted to a sulfate group. Typically, one to about 5, and preferably about 1 to about 4 hydroxyl groups are converted to a sulfate group. To achieve the full advantage of the present invention, about 1 to about 3 hydroxyl groups are converted to sulfate groups. The reaction product typically provides a mixture of sulfated phosphatidylinositols. The above values indicate the average number of sulfate groups present in the sulfated phosphatidylinositol.

In particular, a sulfated phosphatidylinositol is prepared as follows. Phosphatidylinositol (>99% purity) was purchased from Avanti Polar Laboratories, Alabaster, Ala., and used without further purification. The sulfating agent, sulfur trioxide ($SO_3$) in dimethylformamide (DMF), i.e., $SO_3$/DMF, was purchased from Aldrich Chemical Company, Milwaukee, Wis. Anhydrous DMF was purchased from Fisher Scientific, Itasca, Ill. All other reagents were reagent grade chemicals, available from a variety of chemical suppliers.

About 20 mg of phosphatidylinositol was dissolved in a mixture of 2 mL chloroform and 0.5 mL anhydrous DMF. The phosphatidylinositol was sulfated by adding 180 mg of the $SO_3$/DMF complex to the phosphatidylinositol solution, then stirring the resulting solution for 4 hours at 25° C. under a nitrogen blanket. The chloroform then was evaporated using a nitrogen flush, and the resulting mixture was cooled to 4° C. in an ice bath. The reaction was quenched with 2.4 mL of a 4% aqueous sodium hydroxide solution. The sulfated phosphatidylinositols precipitated, and were collected by centrifugation. The sulfated phosphatidylinositols were solubilized in 3 mL of Type II water, and excess sodium sulfate was removed by intercalating the aqueous sulfated phosphatidylinositol solution through an Econo-Pac 10DG desalting column, available from Bio-Rad Laboratories, Hercules, Calif. The effluent was collected, and lyophilized to provide sulfated phosphatidylinositols as an amorphous white powder.

As understood by persons skilled in the art, the degree of sulfation, i.e., the number of hydroxyl groups of phosphatidylinositol converted to sulfate groups, can be controlled by adjusting the amount of $SO_3$/DMF sulfating agent added to the reaction mixture, and by the reaction time. The degree of sulfation can be decreased by decreasing the amount of $SO_3$/DMF added to the reaction mixture or by reducing the reaction time, while the degree of sulfation can be increased by adding excess $SO_3$/DMF to the reaction mixture or by increasing the reaction time.

A variety of analytical and spectroscopic techniques were used to establish the structure of the sulfated phosphatidylinositols (SPI) prepared by the above procedure. For example, the weight percent carbon, hydrogen, nitrogen, and sulfur (i.e., elemental analysis) of starting material, phosphatidylinositol (PI), and reaction product, SPI, were determined. The results summarized in Table 1.

TABLE 1

Elemental Analysis of PI and SPI

| Sample | % Carbon | % Hydrogen | % Nitrogen | % Sulfur |
|---|---|---|---|---|
| PI | 58.99 | 9.21 | 0.12 | — |
| SPI | 36.51 | 6.00 | 0.18 | 12.91 |

The data in Table 1 shows that the weight percent nitrogen in sulfated phosphatidylinositol is essentially identical to the weight percent nitrogen of the phosphatidylinositol starting material. Nitrogen should not be present in PI or SPI, and the low, essentially constant level of nitrogen indicates both the absence of impurities in the PI starting material, and the absence of residual dimethylformamide in the SPI product. In addition, the weight % of sulfur in the compounds increased from an undetectable amount in PI to 12.91% in SPI. The substantial increase in weight percent of sulfur in the SPI product indicates incorporation of sulfate groups into PI starting material.

Phosphatidylinositol and sulfated phosphatidylinositol also were analyzed by Fourier-Transform Infrared Spectroscopy. Solid PI and lyophilized SPI, separately, were homogenized with anhydrous potassium bromide (KBr) into a fine white powder using a mortar and pestle. The resulting solid mixture was compressed to form a clear window using an Infrared Red stainless steel KBr press. An infrared (IR) spectrum then was taken using a Mattson Galaxy 4020 FT-IR Spectrometer. The FT-IR spectra of PI and SPI are set forth in FIG. 1.

The IR spectra of PI, SPI, and heparin (as a reference) were taken. A comparison between the IR spectra of PI and SPI shows that the absorbencies attributed to stretching of carbon-hydrogen single bonds of PI (at 2853 and 2925 $cm^{-1}$) are retained in SPI, which indicates that the hydrocarbon moieties of PI were not hydrolyzed during sulfation. Furthermore, the appearance of a strong absorption at 1259 $cm^{-1}$ in the IR spectrum of SPI, which is not present in the IR spectrum of PI, indicates the presence of sulfate groups ($—OSO_3H$).

The IR spectrum of heparin, an endogenous anionic polysaccharide known to contain sulfate groups, was compared to the IR spectra of PI and SPI. The strong absorption at about 1250 $cm^{-1}$ in the heparin IR spectrum has been identified as the oscillation frequencies of sulfate groups present on the heparin molecule. (See, Bychkov et al., *Biochemistry and Biophysics*, 91(4), 442–445 (1981), and Bychkov et al., *Biochemistry and Biophysics*, 92(12), 680–683 (1981).) Therefore, the presence of a strong absorption peak at about 1250 cm$^{-1}$ in the SPI IR spectrum strongly suggests the presence of sulfate groups. Accordingly, an IR analysis of SPI is consistent with the incorporation of sulfate groups into a PI molecule without compromising the integrity of the PI molecule.

Samples of PI and SPI were analyzed by negative-ion mass spectrometry (MS) using a Finnigan LCQ mass spectrometer. The spectrum is illustrated in FIG. 2 and the results are summarized in Table 2. In a preliminary MS experiment (data not shown), the mass-to-charge ratio for PI was determined to be 833.7 mass units, i.e., m$\mu$. The mass spectrum of SPI shows essentially no evidence for the presence of residual PI. However, significant amounts of species having mass-to-charge ratios of 913, 1015, 1117, and 1219 mass units were detected. Arithmetic differences between any of these species reveals a change of 102 m$\mu$ or multiples of 102 m$\mu$. For example, the difference between 1219 and 1117 is 102 m$\mu$, the difference between 913 and 1015 is 102 m$\mu$, and the difference between 913 and 1117 is 204 m$\mu$. The loss or addition of 102 mass units corresponds to the loss or addition of one sulfate group.

TABLE 2

Mass Spectrum of SPI
MS

| M/z | Molecule |
| --- | --- |
| 833 | PI |
| 913 | Monosulfated PI |
| 1015 | Disulfated PI |
| 1117 | Trisulfated PI |
| 1219 | Tetrasulfated PI |

The 80 mass unit difference between PI (833 m$\mu$) and the 913 m$\mu$ species corresponds to the addition of one sulfate group and the simultaneous loss of one sodium atom. Thus, the 913, 1015, 1117, and 1219 m$\mu$ are assigned to mono-, di-, tri-, and tetrasulfated phosphatidylinositol, respectively. The negative-ion mass spectroscopy assay shows that sulfated phophatidylinositol (SPI) is a mixture of mono-, di-, tri-, and tetrasulfated phosphatidylinositols.

The surface activity of SPI also was determined. In this test, dilutions of SPI were prepared and the surface tension of each solution measured using a Fisher Scientific Surface Tensiometer. Surface tension was plotted as a function of SPI concentration and the results are shown in FIG. 3. The critical micelle concentration (CMC) of SPI was estimated as the minimum concentration at which the surface tension remains constant. For SPI, the CMC is about 0.10 mg/mL. Surface tension measurements using phosphatidylinositol showed no similar surface activity. In fact, addition of water to PI resulted in the formation of phosphatidylinositol liposomes. Accordingly, the addition of sulfate groups to PI alters its aqueous behavior, shifting the tendency of the phospholipid from forming vesicles to forming micelles.

A sulfated phosphatidylinositol of the present invention can be used alone (i.e., in the absence of another therapeutic agent) to treat a disease. The sulfated phosphatidylinositol also can be used in conjunction with another therapeutic agent to both treat a disease, and to act as a component of a drug delivery system for the therapeutic agent. The drug delivery system containing an SPI improves delivery of the therapeutic agent to a target site within an individual.

When used alone or as a component of a pharmaceutical composition, a sulfated phosphatidylinositol can be administered to an individual by a conventional route of administration, including, but not limited to, intravenous, intramuscular, oral, inhalation (pulmonary delivery), nasal, buccal, parenteral, sublingual, transdermal, conjunctival, intraocular, aural, subcutaneous, rectal, vaginal, and topical administration. Oral administration is preferred.

When administered alone or as a component of a pharmaceutical composition, either as a solid or a liquid, a sulfated phosphatidylinositol is administered in admixture with a carrier selected with regard to the intended route of administration and standard pharmaceutical practice. For example, the SPI can be administered orally, buccally, or sublingually, in the form of tablets containing excipients, such as starch or lactose, or in capsules or ovules, either alone or in admixture, with excipients, or in the form of elixirs of suspensions containing flavoring or coloring agents. Such liquid preparations can be prepared with pharmaceutically acceptable additives such as suspending agents (e.g., methylcellulose, a glyceride, or mixtures of glycerides, such as a mixture of apricot kernel oil and PEG-6 esters or mixtures of PEG-8 and caprylic/capric glycerides). A SPI also can be injected parenterally, for example, intravenously, intramuscularly, subcutaneously, or intracoronarily. For parenteral administration, the SPI typically is used in the form of a sterile aqueous solution that can contain other substances, for example, salts, or monosaccharides, such as mannitol or glucose, to make the solution isotonic with blood.

When used alone in therapy, or in conjunction with another therapeutic agent, a sulfated phosphatidylinositol is administered in an amount of about 0.1 to about 1000 mg daily for an average adult (70 kg), as a single dose or in multiple doses, to provide the desired pharmacologic response, such as antiviral activity against HIV.

A benefit of using a sulfated phosphatidylinositol to provide a pharmacologic response is that sulfated phosphatidylinositols have a nominal weight average molecular weight of about 1250 g/mol. A sulfated phosphatidylinositol, therefore, is in the same molecular weight range as many small molecule therapeutic agents, like antibiotics, anticancer drugs, and peptide and protein drugs. In addition, the sulfated phosphatidylinositols not only provide a therapeutic benefit, but also overcome disadvantages associated with using sulfated polymers in therapy, like high cost, difficulty in preparation or isolation, low efficacy and bioavailability, and an anticoagulant effect.

As an additional advantage, a sulfated phosphatidylinositol can be used not only for its therapeutic effects, but also as a component of a drug delivery system in a pharmaceutical composition that contains an additional therapeutic agent. The drug delivery system provides an improved delivery of the therapeutic agent. Such a pharmaceutical composition has the advantages of having a drug delivery system, which includes a sulfated phosphatidylinositol, that more effectively delivers the therapeutic agent to a target site within an individual and that also provides a therapeutic benefit.

Sulfated phosphatidylinositols are useful as a component in a drug delivery system of pharmaceutical compositions because, although the sulfated phosphatidylinositols are derivatives of phosphatidylinositol, the sulfated derivatives retain many of the physiocochemical properties of the native phosphatidylinositol, including an amphiphilic character. Therefore, a sulfated phosphatidylinositol can be utilized in a drug delivery system that further contains an amphiphilic component. Such drug delivery systems include, but are not limited to, liposomes, micelles and mixed micelles, emulsions and microemulsions, gels, liquid crystals, microspheres, and nanoparticles, for example.

An amphiphile utilized with the sulfated phosphatidylinositol is a molecule having a water-soluble (hydrophilic) polar head and a water-insoluble (hydrophobic) organic tail. Examples of amphiphiles include an anionic surfactant, a cationic surfactant, a nonionic surfactant, or a compatible mixture of surfactants. The surfactant also can be an ampholytic or amphoteric surfactant, which have anionic or cationic properties depending upon the pH of the composition.

The amphiphile can be an anionic surfactant, and more particularly any anionic surfactant having a hydrophobic moiety, such as a carbon chain including about 8 to about 30 carbon atoms, and particularly about 12 to about 20 carbon atoms, and further has a hydrophilic moiety, such as sulfate, sulfonate, carbonate, phosphate, or carboxylate. Often, the hydrophobic carbon chain is etherified, such as with ethylene oxide or propylene oxide, to impart a particular physical property, such as increased water solubility or reduced surface tension to the anionic surfactant.

Therefore, suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylaryl sulfonates, alkyl monoglyceride sulfates, alkyl monoglyceride sulfonates, alkyl carbonates, alkyl ether carboxylates, fatty acids, sulfosuccinates, sarcosinates, oxtoxynol or nonoxynol phosphates, taurates, fatty taurides, fatty acid amide polyoxy-ethylene sulfates, isethionates, or mixtures thereof. Additional anionic surfactants are listed in McCutcheon's Emulsifiers and Detergents, 1993 Annuals, (hereafter McCutcheon's), McCutcheon Division, MC Publishing Co., Glen Rock, N.J., pp. 263–266, incorporated herein by reference. Numerous other anionic surfactants, and classes of anionic surfactants, are disclosed in Laughlin et al. U.S. Pat. No. 3,929,678, incorporated herein by reference.

A preferred anionic surfactant is selected from the following classes of surfactants: a $C_8$–$C_{18}$ alkyl sulfate, a $C_8$–$C_{18}$ fatty acid salt, a $C_8$–$C_{18}$ alkyl ether sulfate having one or two moles of ethoxylation, a $C_8$–$C_{18}$ alkamine oxide, a $C_8$–$C_{18}$ alkoyl sarcosinate, a $C_8$–$C_{18}$ sulfoacetate, a $C_8$–$C_{18}$ sulfosuccinate, a $C_8$–$C_{18}$ alkyl diphenyl oxide disulfonate, a $C_8$–$C_{18}$ alkyl carbonate, a $C_8$–$C_{18}$ alpha-olefin sulfonate, a methyl ester sulfonate, and mixtures thereof. The $C_8$–$C_{18}$ alkyl group contains eight to sixteen carbon atoms, and can be straight chain (e.g., lauryl) or branched (e.g., 2-ethylhexyl). The cation of the anionic surfactant can be an alkali metal (preferably sodium or potassium), ammonium, $C_1$–$C_4$ alkylammonium (mono-, di-, tri), or $C_1$–$C_3$ alkanolammonium (mono-, di-, tri-).

The amphiphile also can be a nonionic surfactant. Typically, a nonionic surfactant has a hydrophobic base, such as a long chain alkyl group or an alkylated aryl group, and a hydrophilic chain comprising a sufficient number (i.e., 1 to about 30) of ethoxy and/or propoxy moieties. Examples of classes of nonionic surfactants include ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$–$C_{18}$) acids, condensation products of ethylene oxide with long chain amines or amides, and mixtures thereof.

Exemplary nonionic surfactants include, but are not limited to, methyl gluceth-10, PEG-20 methyl glucose distearate, PEG-20 methyl glucose sesquistearate, $C_{11\text{-}15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$–$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof.

Numerous other nonionic surfactants are disclosed in McCutcheon's Detergents and Emulsifiers, 1993 Annuals, published by McCutcheon Division, MC Publishing Co., Glen Rock, N.J., pp. 1–246 and 266–272; in the *CTFA International Cosmetic Ingredient Dictionary, Fourth Ed.*, Cosmetic, Toiletry and Fragrance Association, Washington, D.C. (1991) (hereinafter the CTFA Dictionary) at pages 1–651; and in the *CTFA Handbook*, at pages 86–94, each incorporated herein by reference.

In addition to anionic and nonionic surfactants, cationic, ampholytic, and amphoteric surfactants can be used as the amphiphile. Ampholytic surfactants can be broadly described as derivatives of secondary and tertiary amines having aliphatic radicals that are straight chain or branched, and wherein one of the aliphatic substituents contains from about 8 to 18 carbon atoms and at least one of the aliphatic substituents contains an anionic water-solubilizing group, e.g., carboxy, sulfonate, or sulfate. Examples of compounds falling within this description are sodium 3-(dodecylamino) propionate, sodium 3-(dodecylamino)-propane-1-sulfonate, sodium 2-(dodecylamino)ethyl sulfate, sodium 2-(dimethylamino)octadecanoate, disodium 3-(N-carboxymethyl-dodecylamino)propane-1-sulfonate, disodium octadecyliminodiacetate, sodium 1-carboxymethyl-2-undecylimidazole, and sodium N,N-bis(2-hydroxy-ethyl)-2-sulfato-3-dodecoxypropylamine.

More particularly, one class of ampholytic surfactants include sarcosinates and taurates having the general structural formula

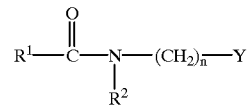

wherein $R^1$ is $C_{11}$ through $C_{21}$ alkyl, $R^2$ is hydrogen or $C_1$–$C_2$ alkyl, Y is $CO_2M$ or $SO_3M$, M is an alkali metal, and n is a number 1 through 3.

Another class of ampholytic surfactants is the amide sulfosuccinates having the structural formula

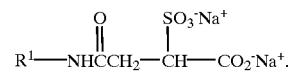

The following classes of ampholytic surfactants also can be used:

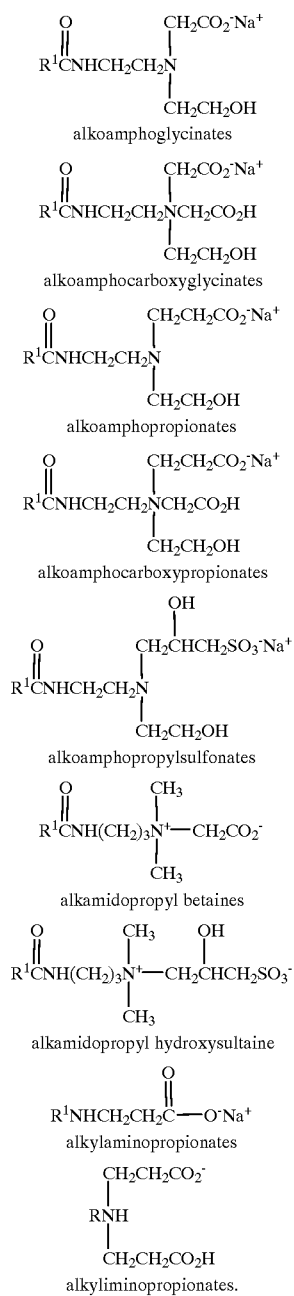

alkoamphoglycinates alkoamphocarboxyglycinates alkoamphopropionates alkoamphocarboxypropionates alkoamphopropylsulfonates alkamidopropyl betaines alkamidopropyl hydroxysultaine alkylaminopropionates alkyliminopropionates.

Additional classes of ampholytic surfactants include the phosphobetaines and the phosphitaines.

Specific, nonlimiting examples of ampholytic surfactants useful in the present invention are sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl)carboxymethylbetaine, oleyldimethylgammacarboxypropylbetaine, lauryl-bis-(2-hydroxy-propyl)-carboxyethylbetaine, cocoamidodimethylpropylsultaine, stearylamidodimethylpropylsultaine, laurylamido-bis-(2-hydroxyethyl)propylsultaine, disodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof.

Once the sulfated phosphatidylinositol is integrated into the drug delivery system, the drug delivery system can be used in pharmaceutical compositions to deliver a variety of drugs, including, but not limited to, peptides, proteins, antivirals, antibacterials, antifungals, antineoplastics, antiprotozoals, antiarthritics, and antiinflammatory agents, to a target site within an individual.

Therapeutic agents that can be incorporated into the pharmaceutical composition include, but are not limited to, antiinflammatory drugs, like tereofenamate, proglumetacin, tiaramide, apazone, benzpiperylon, pipebuzone, ramifenazone, and methotrexate; anti-infective drugs, like isoniazid, polymyxin, bacitracin, tuberactionomycin, and ethryomycin; antiarthritis drugs, like penicillamine, chloroquine phosphate, glucosamine, and hydroxychloroquine; diabetes drugs, like insulin, and glycogen; and anticancer drugs, like cyclophosphamide, interferon $\alpha$, interferon $\beta$, interferon $\gamma$, vincristine, and vinblastine. Appropriate doses of such therapeutic agents, for use in conjunction with the drug delivery system, are readily determined by persons skilled in the art.

A drug delivery system of the present invention comprises a sulfated phosphatidylinositol and an amphiphilic compound. The drug delivery system typically is in the form of a liposome, but also can be, for example, an emulsion, microemulsion, micelle, mixed micelle, gel, liquid crystal, microsphere, or nanoparticle.

The drug delivery system comprises a sulfated phosphatidylinositol and an amphilic compound in a weight ratio of SPI to amphiphilic compound of about 5 to 95 to about 95 to 5, and preferably about 15 to 85 to about 85 to 15. To achieve the full advantage of the present invention, the weight ratio is about 75 to 25 to about 25 to 75.

A liposome is a membrane vesicle prepared from a sulfated phosphatidylinositol and a phospholipid. Structurally, a liposome is a bilayer spherical membrane having polar ends of phospholipids in one layer forming the external surface of the spherical membrane and the polar ends of phospholipids in a second layer forming the internal surface of the spherical membrane. The nonpolar, hydrophobic tails of the phospholpeds in the two layers align to form the interior of the bilayer membrane.

The bilayer liposomes can microencapsulate compounds, and transport the compounds through environments wherein the compound normally is degraded. Liposomes, therefore, are useful as drug delivery systems.

For example, a drug delivery system is prepared by forming a conventional liposome from a phospholipid and a sulfated phosphatidylinositol. The phospholipids used to form a liposome useful in the present invention are not limited. The liposome, therefore, can be prepared by conventional techniques from phosphatidylethanolamine (i.e., cephalin), phosphatidylcholine (i.e., lecithin), phosphatidylserine, phosphatidylinositol, phostidylglycerol, 3'-O-lysylphosphatidylglycerol, cardiolipin, sphingomyelin, and mixtures thereof, for example. In general, the phospholipid can be any glyceride esterified by $C_6$–$C_{24}$ fatty acids at the 1,2-positions and having a phosphoric acid ester residue at the 3-position. It is not necessary to use a purified phospholipid to form the liposome. Commercial phospholipids, like commercial lecithin, can be used in the present invention, and, therefore, provide economies in providing a drug delivery system of the present invention.

To illustrate a drug delivery system of the present invention, several liposome formulations were prepared in which a portion of the normal phospholipid bilayer (i.e., about 5% to about 50% by weight) was replaced with a sulfated phosphatidylinositol. For example, commercially available lecithin (i.e., phospholipon 80, available from American Lecithin Company, Oxford, Conn.) was dissolved in ethanol or chloroform, then the resulting solution was dried to a thin film in a round bottom flask. The film then was hydrated with an aqueous solution of sulfated phosphatidylinositols. The resulting large, multilamellar liposomes were reduced in size by sonication for 5 minutes, followed by repeated extrusion through a 200 nm membrane, to produce smaller uni- and multilamellar liposomes incorporating sulfated phosphatidylinositols having an average diameter of 200 nm.

The resulting polysulfated phospholipid (i.e., PSL) was assayed by gel permeation chromatography. Colloidal solutions of the PSL, a conventional liposome, and SPI alone were intercalated through a 1×20 cm column packed with Sepharose 6B, and eluted with phosphate-buffered saline. The eluent was collected in 1.0 mL aliquots, and each aliquot analyzed for the presence of phospholipid and SPI. The results are illustrated in FIG. 6. The data indicates that conventional liposomes elutes between fraction 5 and fraction 9 (solid circles). Furthermore, PSL also elutes between fraction 5 and fraction 9 (open circles). However, SPI alone elutes between fraction 9 and fraction 17 (solid squares). Because sepharose 6B separates substances based on molecular weight, with larger molecular material eluting first, and PSL exhibits the same elution profile as conventional liposomes. These results confirm that the SPI is an integral component of the PSL phospholipid bilayer as opposed to being simply dissolved in the aqueous medium.

The particle size and zeta potential (i.e., surface charge) of liposomes containing sulfated phosphatidylinositols were measured and compared to conventional liposomes free of sulfated phosphatidylinositols. The test results are summarized below in Table 2.

TABLE 2

| Sample | Mean Diameter (nm) | Zeta Potential (mV) |
|---|---|---|
| Conventional Liposome | 234.7 | −77.8 |
| PSL Liposomes | 233.4 | −92.2 |

The mean diameter and zeta potential (surface charge) of conventional liposomes and PSL were determined following extrusion through a 200 nm polycarbonate membrane. The results summarized in Table 2 indicate that incorporation of a sulfated phosphatidylinositol into the lipid bilayer of a liposome does not effect particle diameter, but the surface charge of liposome becomes significantly more negative. The increase in the negative character of the liposome surface is attributed to the presence of a plurality of sulfate groups on the vesicle surface. Gel permeation chromatography and zeta potential measurements confirm that when formulated as a liposome, an SPI behaves as a phospholipid and participates in bilayer formation.

The drug delivery system prepared in the above example can be formulated with a water-soluble drug, a water-insoluble drug, or a mixture thereof. A water-soluble drug is encapsulated by the drug delivery system, whereas a water-insoluble drug is positioned in the hydrophobic bilayer of the system.

Such a drug delivery system can be used in a pharmaceutical composition for the administration of a therapeutic agent, e.g., a drug, to an individual. The pharmaceutical composition, in addition to the drug delivery system (i.e., the sulfated phosphatidylinositol and amphiphilic compound) contains a therapeutic agent, including, but not limited to, peptides, proteins, antivirals, such as azidothymidine, antibacterials, antifungals, antineoplastics, antiprotozoals, antiarthritics, and antiinflammatory agents.

In particular, an aqueous pharmaceutical composition containing a therapeutic agent and a present drug delivery system can be formed by admixing the therapeutic agent and the drug delivery system. Such aqueous compositions can be administered by injection or orally. Another important embodiment of the present invention is a solid pharmaceutical composition containing a therapeutic agent and a drug delivery system, in a lyophilized form, that can be used to administer the therapeutic agent orally. In this embodiment, an aqueous pharmaceutical composition is formed, and the liquid composition then is lyophilized by conventional techniques.

The specific physicochemical properties of the drug delivery system can be adjusted by a judicious selection of the amphiphilic compound, e.g., the phospholipid, used to form the drug delivery system, by the weight ratio of SPI to amphiphilic compound, and by the incubation time. The proper selection of a drug delivery system also permits the delivery of a therapeutic agent to a particular target site. The drug delivery system, therefore, can more effectively deliver a drug or therapeutic agent to the target site to act against the disease of concern.

To demonstrate the ability of a sulfated phosphatidylinositol to provide a pharmacologic response, the in vitro anti-HIV activities of a sulfated phosphatidylinositol (SPI), polysulfated liposomes (PSLs), and drug loaded PSLs were evaluated as follows. A number of formulations of SPI and PSLs were prepared and their in vitro anti-HIV activity determined by the National Cancer Institute at the National Institutes of Health, Bethesda, Md., using the method of Gustafson et al, *J. Nat. Can. Inst.*, 81(16), 1254–1258 (1989). Varying concentrations of each formulation were mixed with cultured human lymphoblastoid cells, then cocultivated with host cells chronically infected with HIV-1 virus at 37° C. After 7 days, the cell culture is incubated with a mixture of tetrazolium salt XTT and phenazine methylsulfate for 4 hours. Viable, uninfected, and proliferating lymphoblastoid cells metabolize this mixture to the chromophore formazan, while infected cells do not. Formazan absorbs visible light at 450 nm. Therefore, the amount of formazan produced is a direct measurement of cell viability and, consequently, an estimate of the anti-HIV activity of each formulation. Formazan production in normal, uninfected cells is labelled as control.

The results are summarized in FIGS. 5–7, and indicate that an SPI and a liposome containing SPI (i.e., a PSL) protect human lymphoblastoid cells from HIV-1 infection at relatively low concentrations, i.e., at an $ED_{50}$ (effective dose) of about 15 µg/mL and about 25 µg/mL, respectively. Positive anti-HIV results are observed at about 10 µg/mL and about 20 µg/mL.

In particular, the following compositions were assayed for anti-HIV activity. The data and effective concentration ($ED_{50}$), i.e., the minimum concentration that protects 50% of the cells against infection, of each composition are summarized in FIGS. 5–7 and the results summarized in Table 3. Control values were obtained by incubating lymphoblastoid cells with each formulation in the absence of HIV.

1. Sulfated Phosphatidylinositol Alone (FIG. 5) $EC_5$= 11.55 µg/mL
2. Conventional Liposomes (FIG. 6) $EC_{50}$=180.32 µg/mL
3. Polysulfated Liposomes (PSLs) (FIG. 7).

Three PSL compositions were prepared and tested for anti-HIV activity. The amount of phospholipid in each composition is as follows:

| Formulation | Weight % Phospholipon 80 | Weight % SPI |
|---|---|---|
| PSL (L) | 90 | 10 |
| PSL (M) | 60 | 40 |
| PSL (H) | 40 | 60 |

Although the weight percent of SPI in each formulation was different, the in vitro evaluation was normalized to the amount of SPI in each formulation, as opposed to the total phospholipid concentration. On the basis of SPI content, the results for the three PSL compositions were essentially identical, with an average $EC_{50}$ of 17.10 µg/mL.

TABLE 3

Antiviral Activities ($EC_{50}$) of SPI and Related Formulations

| Sample | $EC_{50}$ (µg/ml) |
|---|---|
| SPI | 11.55 |
| Conventional Liposome | 180.32 |
| PSL(L) | 17.51 |
| PSL(M) | 16.38 |
| PSL(H) | 17.40 |
| Delaviridine | 0.031 |
| CL-D | 0.035 |
| PSL-D | 0.012 |

Delaviridine mesylate is a commercial anti-HIV drug available from BIOMOL Research Laboratories, Inc. (Plymouth Meeting, Pa). Three delaviridine compositions were prepared for anti-HIV testing: delaviridine alone, delaviridine encapsulated in a conventional liposome, and delaviridine encapsulated in a PSL. The EC, values for each formulation are summarized in Table 3. Delaviridine alone and delaviridine encapsulated in a conventional liposome exhibit similar anti-HIV activity. However, delaviridine encapsulated in a PSL exhibits a three-fold increase in activity. This increase has been attributed to a synergistic effect between the drug and PSL.

The above tests show that SPI alone ossesses potent anti-HIV activity, whereas conventional liposomes possess minimal anti-HIV activity. PSLs (i.e., conventional liposomes in which a percentage of the bilayer comprises an SPI) exhibit anti-HIV activity equivalent to SPI alone, and encapsulation of a commercial anti-HIV drug in a PSL provides a composition having a synergistic anti-HIV activity.

Many modifications and variations of the invention as hereinbefore set forth can be made without departing from the spirit and scope thereof, and only such limitations should be imposed as are indicated by the appended claims.

What is claimed is:

1. A sulfated phosphatidylinositol having the structure

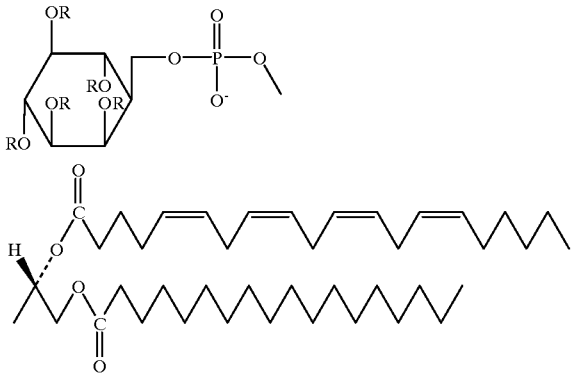

wherein R, independently, is H, $SO_3H$, or $SO^-_3$, and wherein one to five R groups are $SO_3H$ or $SO^-_3$.

2. The sulfated phosphatidylinositol of claim 1 wherein one to four R groups are $SO_3H$ or $SO^-_3$.

3. The sulfated phosphatidylinositol of claim 1 wherein one to three R groups are $SO_3H$ or $SO^-_3$.

4. A compound selected from the group consisting of a monosulfated phosphatidylinositol, a disulfated phosphatidylinositol, a trisulfated phosphatidylinositol, a tetrasulfated phosphatidylinositol, a pentasulfated phosphatidylinositol, and mixtures thereof.

5. A composition comprising a sulfated phosphatidylinositol of claim 1 and a carrier.

6. A composition comprising a sulfated phosphatidylinositol of claim 1 and a therapeutic agent.

7. The composition of claim 6 wherein the therapeutic agent is selected from the group consisting of a peptide, a protein, an antiviral, an antibacterial, an antifungal, an antineoplastic, an antiprotozoal, an antiarthritic, and an antiinflammatory.

8. A composition comprising a sulfated phophatidylinositol of claim 1 and an amphiphile.

9. The composition of claim 8 wherein the amphiphile is selected from the group consisting of an anionic surfactant, a nonionic surfactant, a cationic surfactant, an ampholytic surfactant, an amphoteric surfactant, and mixtures thereof.

10. The composition of claim 8 wherein the amphiphile comprises a phospholipid.

11. The composition of claim 10 wherein the phospholipid is selected from the group consisting of phosphatidylethanolamine, lecithin, phosphatidylserine, phosphatidylinositol, phostidylglycerol, 3'-O-lysylphosphatidylglycerol, cardiolipin, sphingomyelin, and mixtures thereof.

12. A drug composition comprising:
 (a) a drug, and
 (b) a drug delivery system comprising a sulfated phosphatidylinositol of claim 1.

13. The composition of claim 12 wherein the drug is selected from the group consisting of a peptide, a protein, an antiviral, an antibacterial, an antifungal, an antineoplastic, an antiprotozoal, an antiarthritic, and an antiinflammatory.

14. The composition of claim 12 wherein the drug is selected from the group consisting of tereofenamate, proglumetacin, tiaramide, apazone, benzpiperylon, pipebuzone, ramifenazone, methotrexate, isoniazid, polymyxin, bacitracin, tuberactionomycin, ethryomycin, pencillamine, chloroquine phosphate, glucosamine, hydroxychloroquine, insulin, glycogen, cyclophosphamide, interferon α, interferon β, interferon γ, vincristine, delaviridine, and vinblastine.

15. A drug composition comprising:
   (a) a drug; and
   (b) a drug-delivery system, said drug-delivery system comprising:
      (i) a sulfated phophatidylinositol of claim 1, and
      (ii) an amphiphilic compound.

16. The composition of claim 15 wherein the drug-delivery system contains the sulfated phosphatidylinositol and the amphiphilic compound in a weight ratio of about 5 to 95 to about 95 to 5.

17. The composition of claim 15 wherein the drug-delivery system is in the form of a liposome, a micelle, a mixed micelle, an emulsion, a microemulsion, a gel, a liquid crystal, a microsphere, or a nanoparticle.

18. The composition of claim 15 wherein amphilic compound comprises an anionic surfactant, a nonionic surfactant, a cationic surfactant, an amphoteric surfactant, an ampholytic surfactant, or a mixture thereof.

19. The composition of claim 15 wherein the amphilic compound comprises a phospholipid.

20. The composition of claim 19 wherein phospholipid is selected from the group consisting of phosphatidylethanolamine, lecithin, phosphatidylserine, phosphatidylinositol, phostidylglycerol, 3'-O-lysylphosphatidylglycerol, cardiolipin, sphingomyelin, and mixtures thereof.

21. The composition of claim 15 wherein the composition is lyophilized.

22. The composition of claim 15 wherein the composition is a liquid.

23. A method of treating a disease comprising administering a therapeutically effective amount of a drug composition to an individual, said composition comprising:
   (a) a drug capable of treating the disease, and
   (b) a drug delivery system comprising a sulfated phosphatidylinositol of claim 1.

24. The method of claim 23 wherein the drug-delivery system further comprises an amphiphilic compound.

25. The method of claim 24 wherein the amphiphilic compound comprises a phospholipid.

26. The method of claim 24 wherein the amphiphilic compound comprises lecithin.

27. The method of claim 23 wherein the disease is an HIV infection.

28. The method of claim 26 wherein the drug is delaviridine mesylate.

29. The method of claim 23 wherein the composition is administered by injection.

30. The method of claim 23 wherein the composition is administered orally.

31. A method of treating an HIV infection comprising administering a therapeutically effective amount of a sulfated phosphatidylinositol of claim 1 to an individual, wherein the sulfated phosphatidylinositol is administered as a component of a drug delivery system.

32. The method of claim 31 further comprising administering a therapeutic amount of delaviridine.

33. The method of claim 31 wherein the drug delivery system further comprises an amphiphile.

34. The method of claim 33 wherein the amphiphile comprises a phospholipid.

* * * * *

UNITED STATES PATENT AND TRADEMARK OFFICE
CERTIFICATE OF CORRECTION

PATENT NO. : 6,316,424 B1
DATED : November 13, 2001
INVENTOR(S) : Dadey et al.

Page 1 of 1

It is certified that error appears in the above-identified patent and that said Letters Patent is hereby corrected as shown below:

Column 15,
Line 58, "EC" should be -- $EC_{50}$ --.
Line 65, "ossesses" should be -- possesses --.

Column 17,
Line 16, "phophatidylinositol" should be -- phosphatidylinositol --.

Signed and Sealed this

Twenty-eighth Day of May, 2002

Attest:

JAMES E. ROGAN
*Attesting Officer*    *Director of the United States Patent and Trademark Office*